Dec. 5, 1944. C. HARTGERINK Plant Pat. 647
ROSE PLANT
Filed Aug. 4, 1944
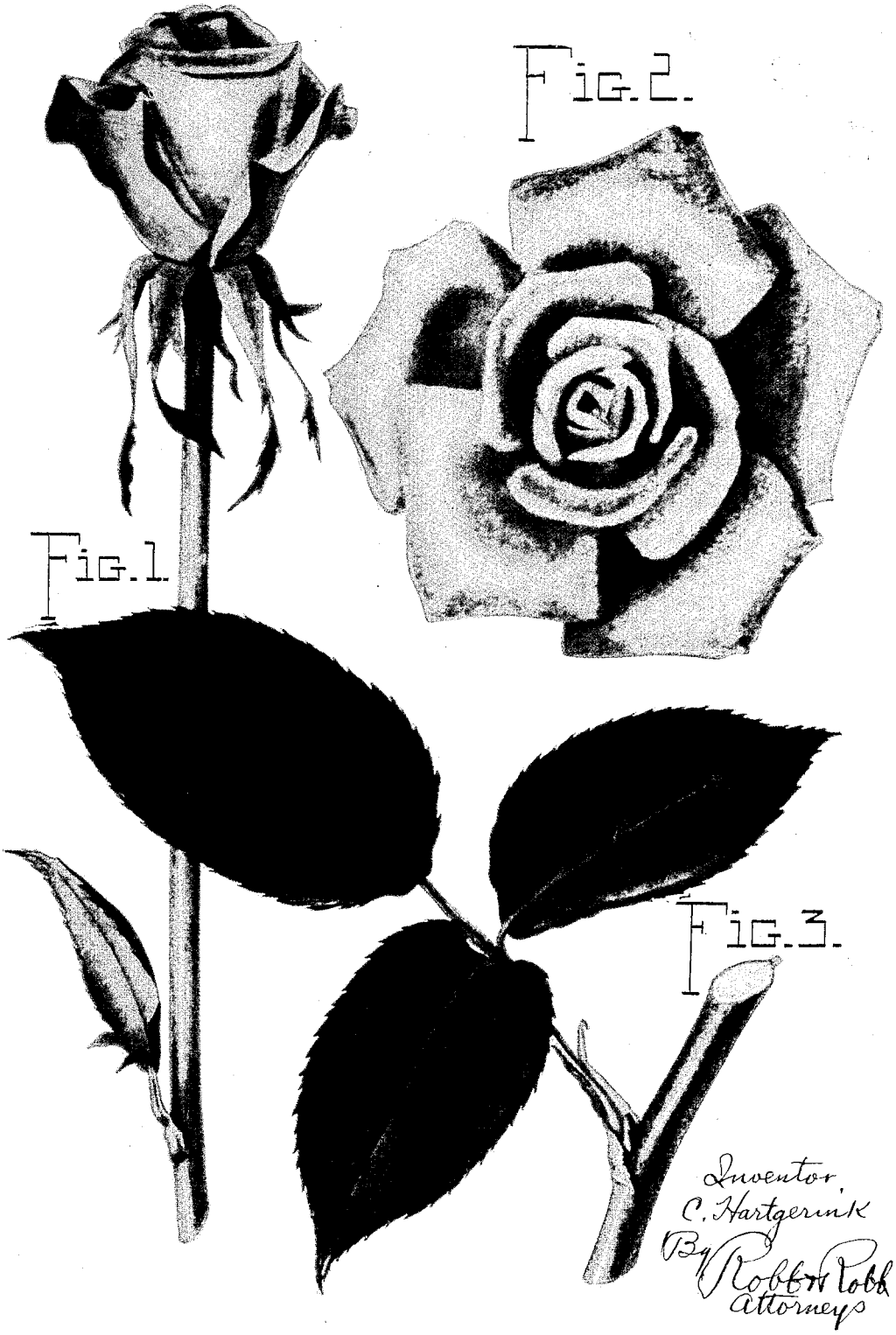

Patented Dec. 5, 1944

Plant Pat. 647

UNITED STATES PATENT OFFICE

647

ROSE PLANT

Conrad Hartgerink, West Los Angeles, Calif., assignor to Armacost & Royston, Inc., West Los Angeles, Calif., a corporation of California Application August 4, 1944, Serial No. 548,050

1 Claim. (Cl. 47—61)

This discovery relates to a new and distinct variety of rose plant originating as a sport of the well-known variety "Better Times."

This new variety resembles its parent, when grown under comparable conditions, with respect to the nature of color of its blossoms, number of petals and lasting quality, but differs from it importantly with respect to habit, its extreme vigor and healthfulness. Due to this extreme vigor of growth of the new rose, the plant produces a grater percentage of long, stronger stems than the parent, fewer thorns, and there is a tendency on some of the canes to make leaves in clusters of two or three instead of five.

In connection with the extra vigor of the new variety, it may be noted that the plants average almost twice the height of the parent plants and at the same time bear a large quantity of excellent, high-quality, long-stemmed roses. Some of the plants at least, from observation of both varieties mentioned, budded at the same time, and grown under the same conditions of water and fertilization, would average many more flowers per plant than "Better Times," as well as a greater degree of thornlessness.

As is well known, color characteristics vary not only with the season, but also with the climate, soil and other factors, and, therefore, in connection with the accompanying illustrations of the new variety, the endeavor was to show the color as nearly as possible at the time and place and under the conditions existing when the observations hereinafter referred to were made.

In the accompanying illustrations—

Figure 1 shows a side elevation of a specimen flower of this new variety partly open, and long stem on which it was borne;

Fig. 2 is a top plan view of a specimen flower in the full open stage of development; and Figure 3 shows a typical foliage group of three leaves.

Asexual reproduction of this new variety shows the foregoing characteristics come true to form and are established.

The following is a detailed description of the new variety, color terminology referring to dictionary definition, except where otherwise indicated by standard chart designations:

Type: Half hardy; tall bush; greenhouse; sport; for cut flowers.

Class: Hybrid tea.

Discovery: At West Los Angeles, California.

*Parent.*—"Better Times." Noticeably tall, vigorous growth as compared with original "Better Times" growing in the same bed.

Propagation: Holds its distinguishing characteristics through succeeding propagations by grafting and budding.

*Flower*

Locality where grown: West Los Angeles, California.

Flowers borne: Generally singly to stem; on strong, long stems.

Quantity of bloom: Free in greenhouse.

Continuity: Continuous.

Fragrance: Moderate; sweetbriar.

Bud:

*Peduncle.*—Long; medium heavy; stiff; light green; almost smooth; few red prickles.

*Before calyx breaks.*—*Size*—medium large. *Form*—Pointed, with a conspicuous neck; foliaceous appendages on the surface of the bud; with much-cut foliaceous parts extending beyond the tip of the bud equal to more than its length.

*As calyx breaks.*—*Color*—Carmine (Ridgway's Color Standard, Plate I).

*As first petal opens.*—*Size*—medium. *Form*—pointed. *Color*—outside—Carmine (Ridgway's Color Standard, Plate I); inside—slightly darker. *Opening*—opens up well; retarded by cold weather.

Bloom:

*Size.*—When fully open, large; 4½ to 5¼ inches.

*Petalage.*—Double; from 64 to 68 petals arranged regularly.

*Form.*—High center at first; becoming globular; petals remaining at first loosely rolled outward; becoming later, at maturity, very loosely cupped and rolled outward.

Petals: Thick; with inside velvety and outside satiny.

*Shape.*—Outside—obovate; with one notch. Intermediate—obovate; with one notch. Inside—obovate; with one notch.

This description of a newly opened flower was made from a rose grown in a greenhouse during the month of June, 1944, at West Los Angeles, California:

*Color.*—(Based on Horticultural Color Chart II.) *Outside petal*—outside surface—Chrysanthemum Crimson, 824/3, page 169; inside surface—Chrysanthemum Crimson, 824/1, page 169. *Intermediate petal*—outside and inside surfaces—shade lighter than Chrysanthemum Crimson. *Inner petal*—outside and inside surfaces—shade lighter than Chrysanthemum Crimson.

This description was made from a rose that was open for three days in a greenhouse during the month of June, 1944, at West Los Angeles, California:

*Color.*—*Outside petal*—outside surface—Rose Color (Ridgway's Color Chart, Plate XII); inside surface—Tyrian Rose (Ridgway's Color Chart, Plate XII). *Inside petal*—outside surface—Rose Red (Ridgway's Color Chart, Plate XII); inside surface—Crimson Carmine (Koster, Plate 41).

*General color effect.*—Three days open—the rose becomes lighter, with a slight bluish cast.

*Behavior.*—Drop off cleanly; fading purple. Slightly bluer from cold and wet. Less blue with heat and dryness.

*Flower longevity.*—Grown in greenhouse kept at living room temperatures, 10 days in May.

*Reproductive organs*

Stamens: Medium in number; arranged irregularly about pistils; mixed with petaloids.

Filaments: Medium length; reddish; many; most with anthers.

Anthers: Medium size; yellow; open at various times.

Pollen: Moderately abundant; yellow.

Pistils: Medium in number.

Styles: Very uneven; short to medium; medium heavy; loosely bunched.

Stigma: Greenish.

Ovaries: Protruding from calyx.

Hips: Short; globular; pear-shaped; yellow-reddish; moderately smooth; walls fleshy.

Sepals: Falling soon; moderately long; spear-shaped; recurved.

*Color.*—Inside—Gray; outside—Green.

Seeds: Few; medium size.

*Plant*

Foliage:

*Leaves.*—Compound of 2—3—5 leaflets; abundant; large; very heavy to leathery.

*Leaflets.*—Shape—ovoid with apex acute. Base—obtuse. Margin—simply serrate.

*Color.*—*Mature* — upper surface — Dark Green; under surface — Gray Green. *Young*—upper surface—Very Dark Bronze; under surface—Moderately Dark Bronze.

*Rachis.*—Medium heavy. Upper side — smooth, grooved; under side—moderately smooth.

*Stipules.*—Medium length; narrow; with long points turning out at an angle of 45°, recurved toward the stem.

*Disease.*—Resistant to mildew and blackspot insofar as this is evidenced by absence of any throughout development and establishing of this variety.

Growth:

*Habit.*—Upright; branched.

*Growth.*—Extremely vigorous.

*Canes.*—Heavy.

*Main stems.*—Bright Green. *Thorns*—few; medium length; hooked downward; with short base. *Prickles*—few; Green. *Hairs*—none.

*Branches.*—Bright Green. *Thorns*—few; medium length; hooked downward; with short base. *Prickles*—few; Green. *Hairs*—none.

*New shoots.*—Bright Green. *Thorns*—very few; short; hooked downward; with short base. *Prickles*—few; Green. *Hairs*—none.

I claim:

A new and distinct variety of rose plant, characterized as to novelty by its extreme vigor and healthfulness compared with its parent "Better Times," greater production of flowers per plant on long, stronger stems, and greater degree of thornlessness and tendency to make but two or three leaves, per cluster, instead of five, on some of the canes, substantially as shown and described.

CONRAD HARTGERINK.